United States Patent [19]

Zappel

[11] 4,315,516
[45] Feb. 16, 1982

[54] CONTINUOUS CHAIN FORMED FROM A MULTIPLICITY OF LOOPS FORMED FROM DENTAL FLOSS MATERIAL AND APPARATUS FOR PRODUCING THE SAME

[76] Inventor: Joseph Zappel, 2 Cielo Dr., Scotts Valley, Calif. 95066

[21] Appl. No.: 188,711

[22] Filed: Sep. 19, 1980

[51] Int. Cl.³ .............................................. A61C 15/00
[52] U.S. Cl. ..................................................... 132/90
[58] Field of Search ................................... 132/90-93; 242/76; 131/94

[56] References Cited

U.S. PATENT DOCUMENTS

| | | | |
|---|---|---|---|
| 2,192,789 | 3/1940 | Harter | 242/76 |
| 2,194,879 | 3/1940 | Von Mihaly et al. | 242/76 |
| 2,692,736 | 10/1954 | Hanley | 242/76 |
| 4,013,085 | 3/1977 | Wright | 132/89 |
| 4,249,547 | 2/1981 | Hinzmann | 131/90 |

Primary Examiner—G. E. McNeill
Attorney, Agent, or Firm—John J. Leavitt

[57] ABSTRACT

Presented is an apparatus for manufacturing a chain of connected loops from an indeterminate length of dental floss material. The loops are formed in such a way that the continuous chain of loops may be wound on an appropriate spool and individual loops detached from the continuous chain of such loops for use in flossing the teeth. The apparatus processes two strands of dental floss material in such a manner that adjacent loops are formed and attached to one another by a length of pressure-sensitive tape that adhesively secures the opposite and associated ends of two strands of dental floss material, and discharges the chain of loops thus formed in a continuous maner.

20 Claims, 23 Drawing Figures

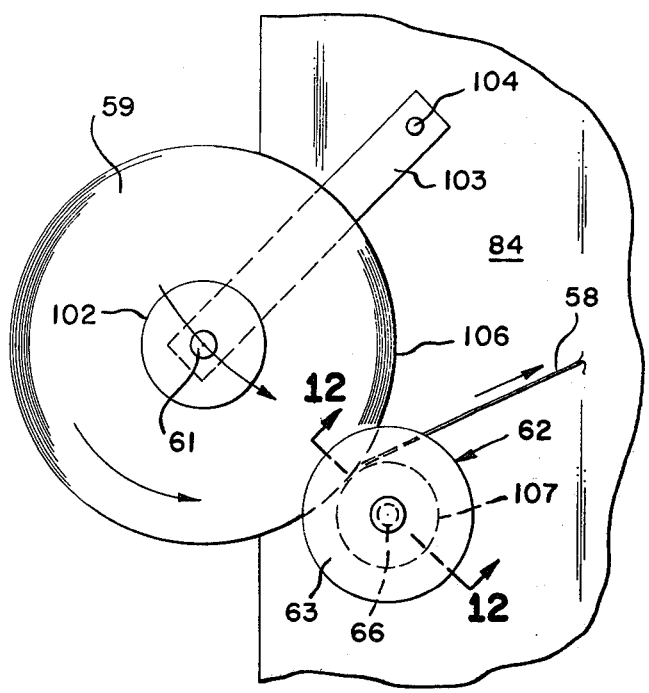
FIG. 11
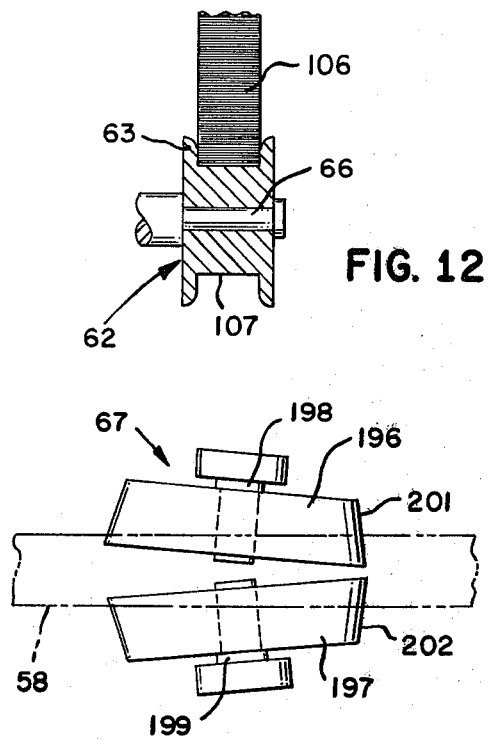
FIG. 12
FIG. 16
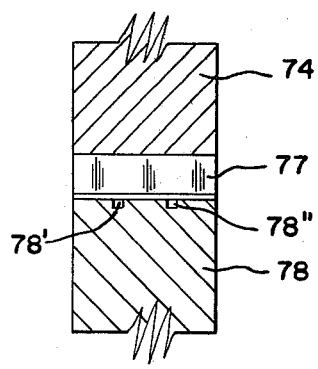
FIG. 18A
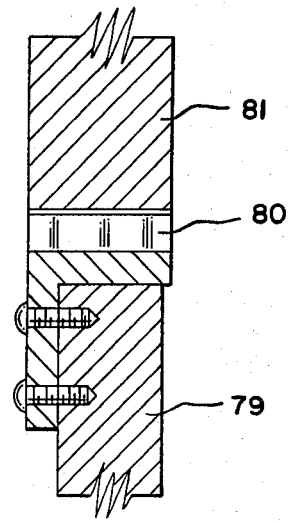
FIG. 19

CONTINUOUS CHAIN FORMED FROM A MULTIPLICITY OF LOOPS FORMED FROM DENTAL FLOSS MATERIAL AND APPARATUS FOR PRODUCING THE SAME

BACKGROUND OF THE INVENTION

1. Field of the Invention

This invention relates to a flossing device for the cleaning of teeth, and particularly to the manufacture of a multiplicity of such devices as a continuous chain of connected and completed loops, each individual loop of the chain being separable from the continuous chain, and to an apparatus for manufacturing such a continuous chain of dental floss loops that are selectively separable from one another.

2. Description of Prior Art

An individual dental floss loop of the type that is described herein as being fabricated as one of a continuous chain of such loops is illustrated, described and claimed in United States Application Ser. No. 956,249 and is illustrated in the attached drawings in its completed and separated form in FIG. 4 hereof. Because of the special configuration of the finished product, namely a completed loop of dental floss formed from two separate strands, associated ends of which are secured together by adhesive tabs, and the necessity of fabricating such a construction in an economical way, the development of special equipment was required to manufacture a continuous chain from a multiplicity of such loops of dental floss material, the chain being formed in such a way that individual loops may be severed or separated from the chain by the user at the time of use, while the chain is fabricated in such a way that it may be adequately packaged for sale to the ultimate consumer in packages containing specific numbers of interconnected yet separable loops, or a specific length of a continuous chain of separable loops. To my knowledge, no existing machinery is available to produce a continuous chain formed from loops of dental floss material.

Because of the relatively low price of a container of dental floss to the ultimate consumer, and because of the enormous volume of dental floss used by the consuming public, it is essential that the apparatus for forming the dental floss loop chain be capable of forming the loop chain in a continuous process, at a high rate of speed, in a form that is aesthetically pleasing and hygienically acceptable to the consuming public. Accordingly, the method of forming the loops and forming a chain of separable loops must lend itself to high speed mechanized production.

Therefore, one of the primary objects of this invention is the provision of an elongated chain or series of interconnected loops arranged in a manner to permit the severability or separation of successive loops from the remaining chain of such loops.

Another object of the invention is the provision of a machine which will join two adjacent strands of dental floss at their ends in such a manner that a closed loop is formed having sufficient strength for the intended use of flossing the teeth.

Still another object of the invention is the provision of a method of joining two adjacent strands of dental floss material in such a manner that interconnected loops are formed from the two adjacent strands, with each loop being separable from adjacent loops while maintaining its integrity as a loop.

Yet another object of the invention is the provision of an apparatus for manufacturing an elongated chain from a series of interconnected dental floss loops in a continuous manner while periodically cutting from the continuous chain a predetermined length formed from a predetermined number of interconnected loops.

The invention possesses other objects and features of advantage, some of which, with the foregoing, will be apparent from the following description and the drawings. It is to be understood, however, that the invention is not limited to the embodiment illustrated and described, since the invention may be embodied in various forms within the scope of the appended claims.

SUMMARY OF THE INVENTION

In terms of broad inclusion, the continuous chain or elongated series of interconnected dental floss loops comprises two strands of dental floss material interconnected at predetermined intervals along their length. In one aspect of the invention, the continuous chain of interconnected loops comprises a pair of parallel dental floss strands or filaments associated end-to-end with similar pairs of elongated strands, with the associated ends of the pairs of strands being interconnected by a tab, the successive tabs being repeated at regular intervals along the elongated chain of interconnected loops between pairs of such loops. In another aspect of the invention, the elongated continuous chain is formed from two elongated pressure sensitive tape strips superimposed over or laminated over associated portions of two separate dental floss strands or filaments that extend loop-like opposite each other in opposite directions beyond opposite edges of the elongated strip of laminated tape to form a pair of opposed loops. Means are provided in the elongated and continuous chain of interconnected loops thus formed for severing or separating one pair of loops from adjacent pairs of loops, and for separating the tape portion between opposed loops to form a single loop from two such opposed loops. Another aspect of this invention comprises the provision of an apparatus for forming an elongated chain from two separate strands of dental floss material, the apparatus being adapted to appropriately bring into spaced parallel juxtaposition selected portions of the two elongated dental floss strands, apply an elongated strip of pressure sensitive tape thereto joining the spaced parallel juxtaposed sections of the dental floss material, thereby and subsequently cutting the tape in one aspect to provide separate tabs joining the opposed ends of the dental floss strands formed into an elongated chain of connected loops, and in another aspect perforating or slitting the tape in such a manner that separate loops may be digitally separated from the elongated chain. Means are provided for resiliently pressing the two opposed pressure sensitive tape strips together to thus sandwich the selected portions of the strands between the two tape strips, for cutting selected slits in the tape at regular intervals correlated to the placement of loops along the tape strips. Means are also provided for cutting predetermined lengths from the continuous chain of interconnected loops of dental floss material, and for wrapping such predetermined lengths on an appropriate spool for packaging.

BRIEF DESCRIPTION OF THE DRAWINGS

FIG. 11 is a fragmentary view in elevation of one of the tape feeding and alignment assemblies.

FIG. 12 is a fragmentary sectional view taken in the plane indicated by the line 12—12 of FIG. 11.

FIG. 16 is a fragmentary plan view of the tape alignment device, taken in the direction of the arrow 16 in FIG. 7.

FIG. 18A is an enlarged fragmentary sectional view taken in the plane indicated by the line 18A—18A in FIG. 18.

FIG. 19 is a fragmentary cross-sectional view illustrating the cut-off wheel or roller and the back-up wheel or roller against which it impinges to cut the tape to predetermined lengths. The view is taken in the plane indicated by the line 19—19 in FIG. 7.

DESCRIPTION OF THE PREFERRED EMBODIMENT

Figure 1:
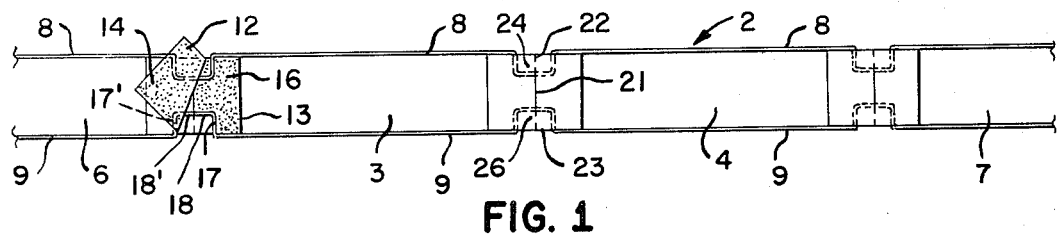
FIG. 1 is a plan view of a portion of an elongated chain of interconnected dental floss loops illustrating two loops interconnected tgether and the interconnection of those two loops with two additional loops arranged in an end-to-end series or relationship. A portion of one of the tabs is peeled back to show the underlying structure.
Figure 3:
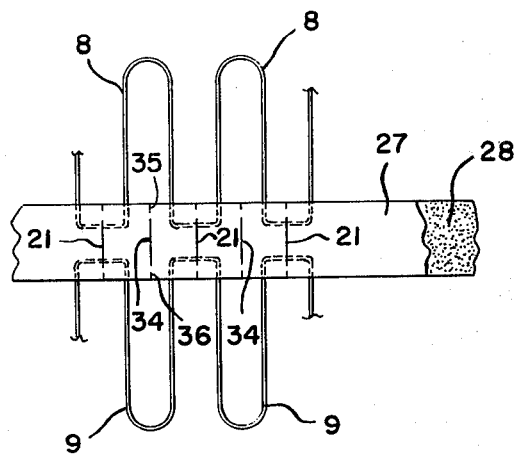
FIG. 3 is a second embodiment of an elongated chain or series of interconnected dental floss loops in which the integrity of the pressure sensitive tape strips that bind the loops together and which maintain the integrity of each separate loop when separated from the elongated chain is retained as an elongated strip for separation of individual loops therefrom by the ultimate user.

In terms of greater detail, the invention embodies two different aspects of a consumer product, one being categorized as an elongated chain or series of interconnected dental floss loops, interconnected by spaced tabs in such a way that individual loops may be separated from the remaining chain or series of loops by the dental floss user. In the other aspect, the invention comprises a chain in which two series of loops are interconnected by an elongated tape in such a way that the loops of each series extend transversely of the longitudinal dimension of the chain or series until such time as a pair of such individual loops is severed from the chain and further separated to form a single dental floss loop. These two aspects of the invention are illustrated in FIGS. 1 and 3 of the drawings. The invention also includes the apparatus by which either one or both of the embodiments of the elongated chain of dental floss loops is formed. This aspect of the invention is illustrated commencing with FIG. 7.

Referring to FIG. 1, a segment of an elongated chain designated generally by the numeral 2 is shown therein and comprises two complete loops 3 and 4 arranged in an end-to-end relationship as illustrated, with the loop 3 being shown arranged in an end-to-end relationship with a portion of loop 6, while the loop 4 is shown arranged in an end-to-end relationship with a loop 7. The loops 6 and 7 are broken away to reduce the length of the figure. Preferably, the elongated chain 2 includes approximately 64 dental floss loops, the chain of 64 loops being wound on an appropriate spool, (not shown) and packaged for sale to the ultimate consumer. The chain 2 of interconnected loops is formed by two separate elongated and continuous filaments or strands of dental floss designated in FIG. 1 by the numerals 8 and 9 which, at predetermined intervals which determine the diameter of each of the loops, are joined by a pair of oppositely facing adhesive tabs 12 and 13, the tabs 12 and 13 being provided with layers of adhesive 14 and 16, respectively, on their facing or opposed surfaces as illustrated in FIG. 1, so that when the two adhesive surfaces 14 and 16 are pressed together they will adhere tightly to each other and laminate and will entrap therebetween and securely hold the associated ends of the filaments 8 and 9 forming the loops 3 and 4 tightly bound between the two adhesive tabs.

The associated ends of the loops are arranged in a mirror image of each other, and the strands or filaments 8 and 9 in the portions caught between the two tabs 12 and 13 are also mirror images of each other with respect to a longitudinal axis centrally disposed with respect to the elongated filaments or strands 8 and 9. Thus, at the occurrence of each pair of laminated tabs 12 and 13, each of the strands 8 and 9 is provided with a transversely extending portion 17 that extends generally perpendicular to the associated strand of which it forms an integral part, and which lies generally perpendicular to one of the side edges of the associated tabs. Integral with the transversely extending portion 17 is a longitudinally extending portion 18 which is aligned with a complementary longitudinally extending portion 18' which constitutes an integral extension of a transverse portion 17' formed on the associated next adjacent loop 6 and specifically the strand 9 thereof.

It should be noted from FIG. 1, that in the completed elongated chain unit, the pairs of tabs 12 and 13 after being pressed together so as to tightly bind the associated ends of associated loops together, are provided with a centrally and transversely extending slit 21 of sufficient length to sever the axially extending portions 18 of associated loops one from the other after the associated ends of the strands 8 and 9 have been caught between the two adhesive tabs 12 and 13. Additionally, each of the pairs of tabs 12-13 is provided with edge slits 22 and 23 which extend transversely inwardly a short distance and which are aligned with the slit 21. The proportions in terms of lengths of the slit 21 and the slits 22 and 23 are such as to leave between the end of the slit 21 and the end of the slit 22 a short section 24 of the adhesive tabs 12-13 which is not severed and which retain one loop attached to the other next adjacent loop. In like manner, a portion 26 of the pair of tabs 12-13 between the inner end of the slit 23 and the outer end of the slit 21 is left uncut so that with the portion 24, two relatively widely spaced yet narrow neck sections are provided that maintain the integrity of the elongated chain and maintain its continuity until such time as a user of a dental floss loop wishes to detach one loop from the next adjacent loop. At that time, all that is required is that the user makes a slight tug on the end loop and it will separate from the remaining chain at the uncut portions 24 and 26.

Figure 2:
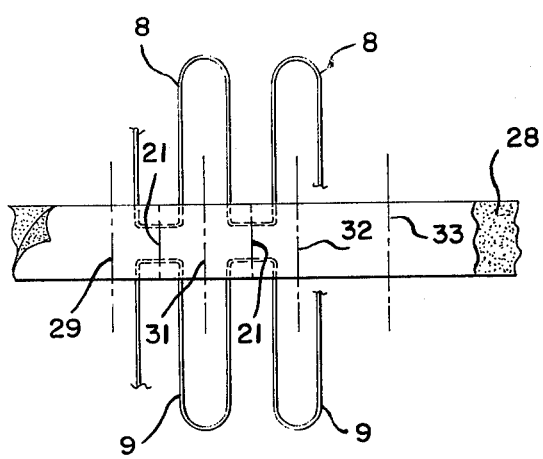
FIG. 2 illustrates in plan a section of the elongated chain of FIG. 1 in an intermediate condition prior to the severing of the tape to form individual and regularly spaced tabs and loops as illustrated in FIG. 1.

It will thus be seen that the completed chain or segment of chain illustrated in FIG. 1, formed from interconnected dental floss loops, lends itself to being mechanically wound on an appropriate spool (not shown) by automatic equipment so that the floss strands 8 and 9 forming each of the loops remain substantially untouched by human hands and therefore are maintained in a substantially uncontaminated condition. It is important to note also that the ultimate configuration of the elongated chain as illustrated in FIG. 1 takes the form illustrated in FIG. 2 at an intermediate point in its fabrication. Thus, tabs 12-13 are severed portions of an elongated and continuous pressure sensitive tape 27 which is provided with a layer of adhesive on one side and a tape 28 of pressure sensitive tape which is aligned with the tape 27 and which is also provided with adhesive on its facing surface so that when the two tapes are pressed and laminated together as they pass through the apparatus illustrated in FIG. 7 they tightly bind portions of the loops in the configuration illustrated in FIG. 2. Thereafter, as the assembly as illustrated in FIG. 2 passes through the apparatus, the now superposed and tightly adherent pair of tapes 27, 28 are cut transversely in the plane indicated by the lines 29, 31, 32 and 33 so as to separate one tab from the other, whereupon extension of the chain will effect elongation thereof and separation of the tabs to their positions as illustrated in FIG. 1. At the time that the assembly as illustrated in FIG. 2 passes through the apparatus, the slits 21, 22 and 23 are formed therein so that upon effecting the transverse cuts 29, 31, 32 and 33, the chain of interconnected loops will be essentially complete.

Figure 4:
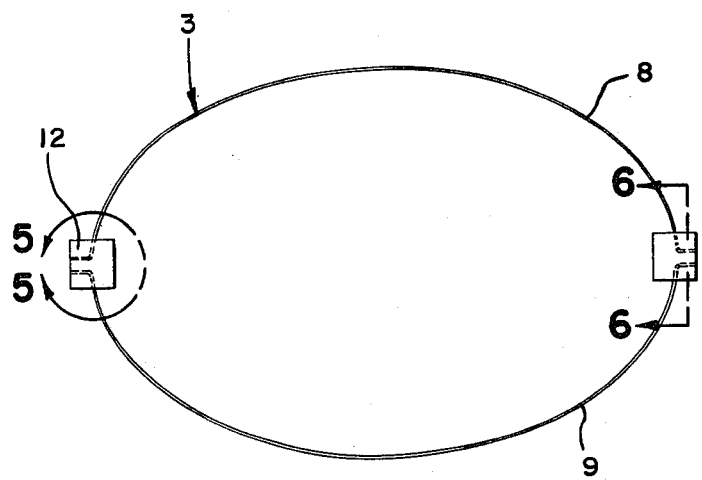
FIG. 4 is a plan view of the completed loop of dental floss material after it has been separated from the elongated chain.
Figure 5:
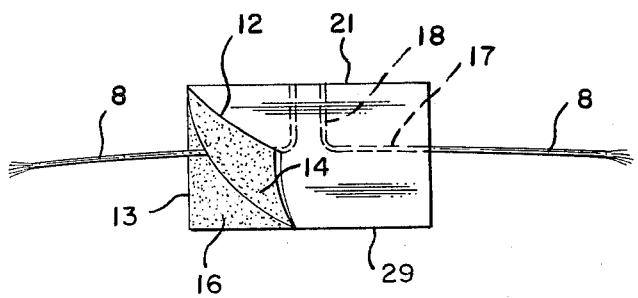
FIG. 5 is a fragmentary plan view taken in the plane indicated by the line 5—5 in FIG. 4.
Figure 6:
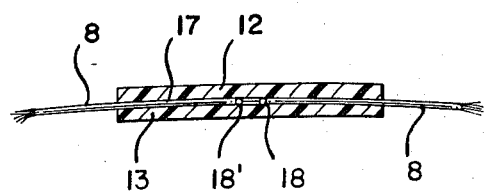
FIG. 6 is a framentary cross sectional view taken in the plane indicated by the line 6—6 in FIG. 4.

The embodiment of the invention illustrated in FIG. 3 is somewhat different from the embodiment of the invention illustrated in FIGS. 1 and 2 in that the integrity of the tapes 27 and 28 are maintained as illustrated and the two tapes are aligned and adhesively pressed together or laminated so as to tightly bind the entrapped portions of the loops 8 and 9. However, in this embodiment of the invention, the slits 21, 22 and 23 are provided as illustrated with respect to FIGS. 1 and 2. Instead of severing the tapes transversely in the planes indicated by the lines 29, 31, 32 and 33 as illustrated in FIG. 2, the embodiment of FIG. 3 provides intermediate slits 34, 35 and 36 similar to the slits 21, 22 and 23. Thus, in its completed form, the elongated chain as illustrated by the portion thereof in FIG. 3 is wound in the form illustrated to form a roll having transversely extending loops. Such roll is then appropriately packaged so that individual loops may be dispensed therefrom with the user tugging on the first emerging loop so that the loop separates at the slits 21, 22 and 23 so as to disengage a loop from the next succeeding loop and then subsequently separating the tape again at the slits 34, 35 and 36 so as to form a simple completed loop in the form illustrated in FIG. 4. It should be understod that with both of the embodiments illustrated in FIGS. 1 and 3, the end result or end product adapted for use in flossing teeth will appear as in FIG. 4.

Figure 7:
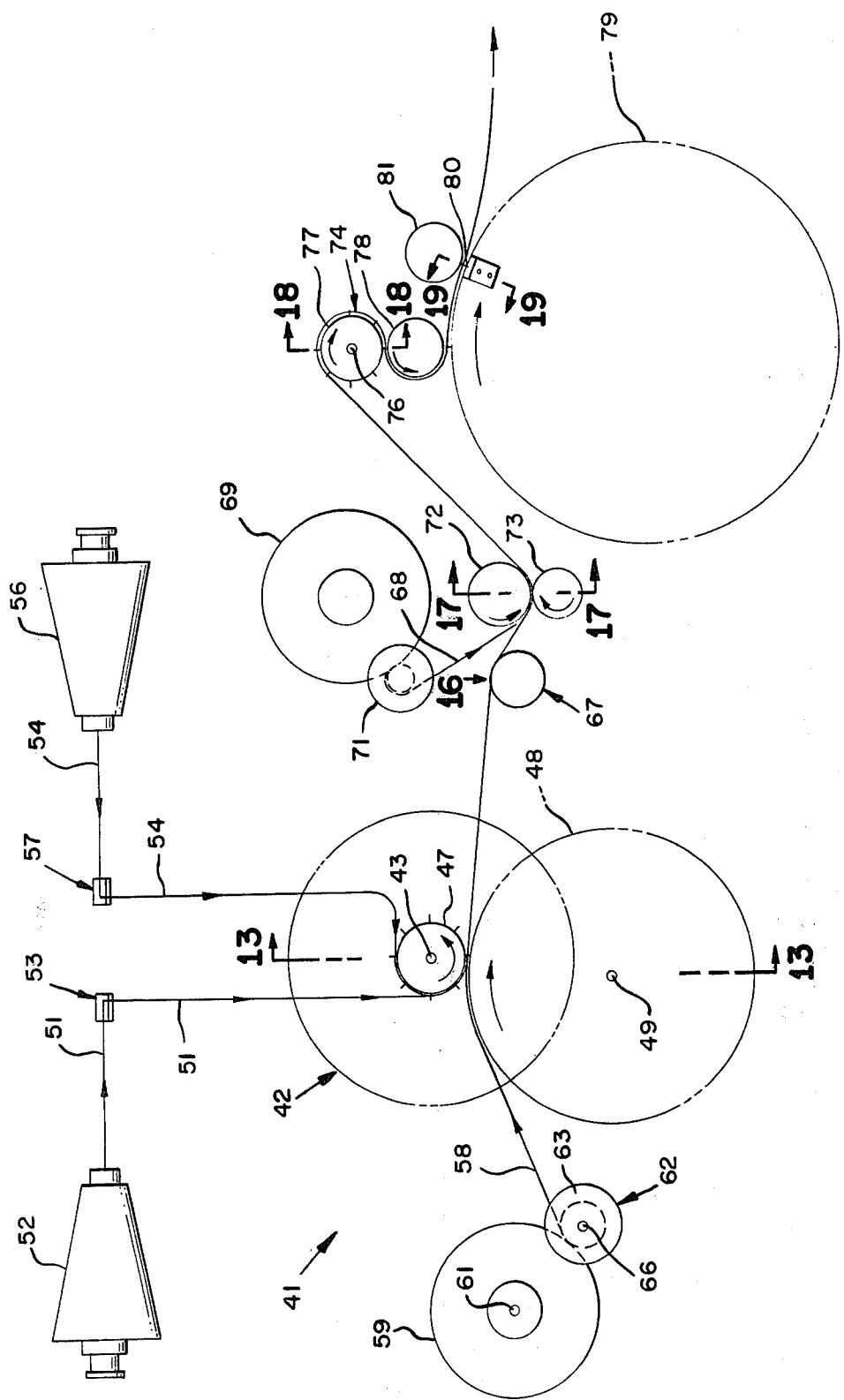
FIG. 7 is a schematic view illustrating the apparatus for converting two separate strands or filaments of dental floss material feeding from two separate sources into an elongated chain of interconnected loops of dental floss material, individual loops being separable from the remaining chain by the user of the floss material.
Figure 13:
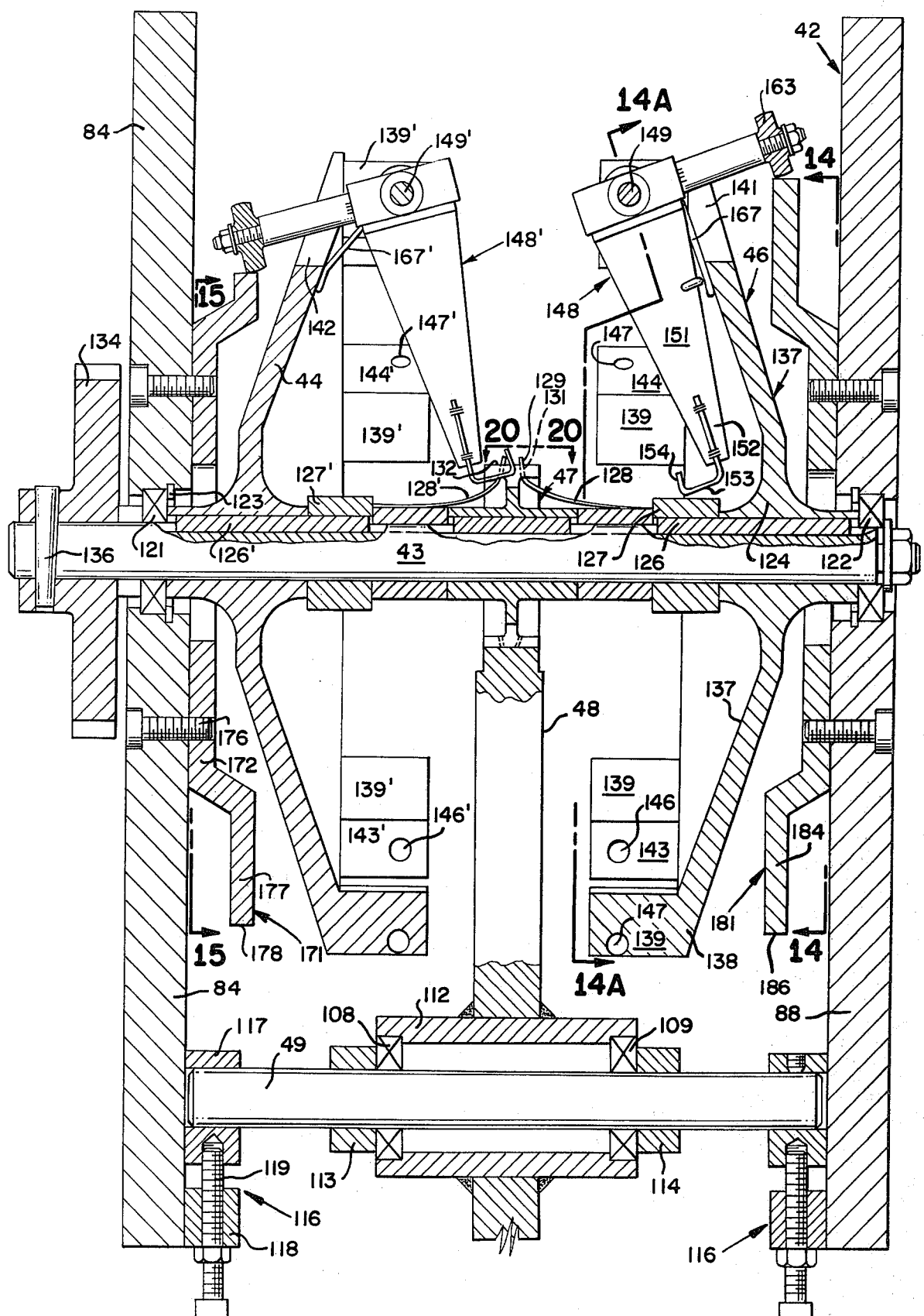
FIG. 13 is a fragmentary vertical cross-sectional view taken in the plane indicated by the line 13—13 in FIG. 7, illustrating the loop puller assembly, portions of which have been omitted for clarity, the impression or cog wheel and a portion of the back-up wheel.
Figure 14:
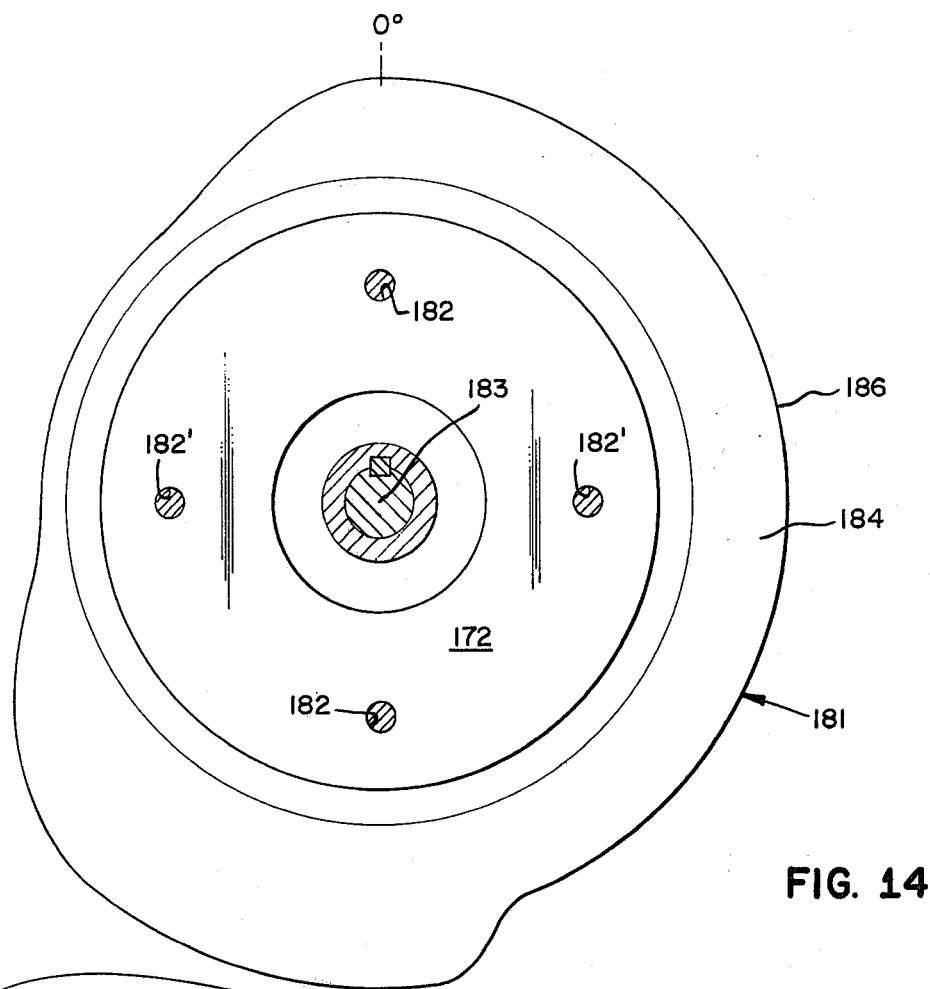
FIG. 14 is a fragmentary vertical sectional view taken in the plane indicated by the line 14—14 in FIG. 13, and illustrating the configuration and orientation of the right cam.
Figure 14A:
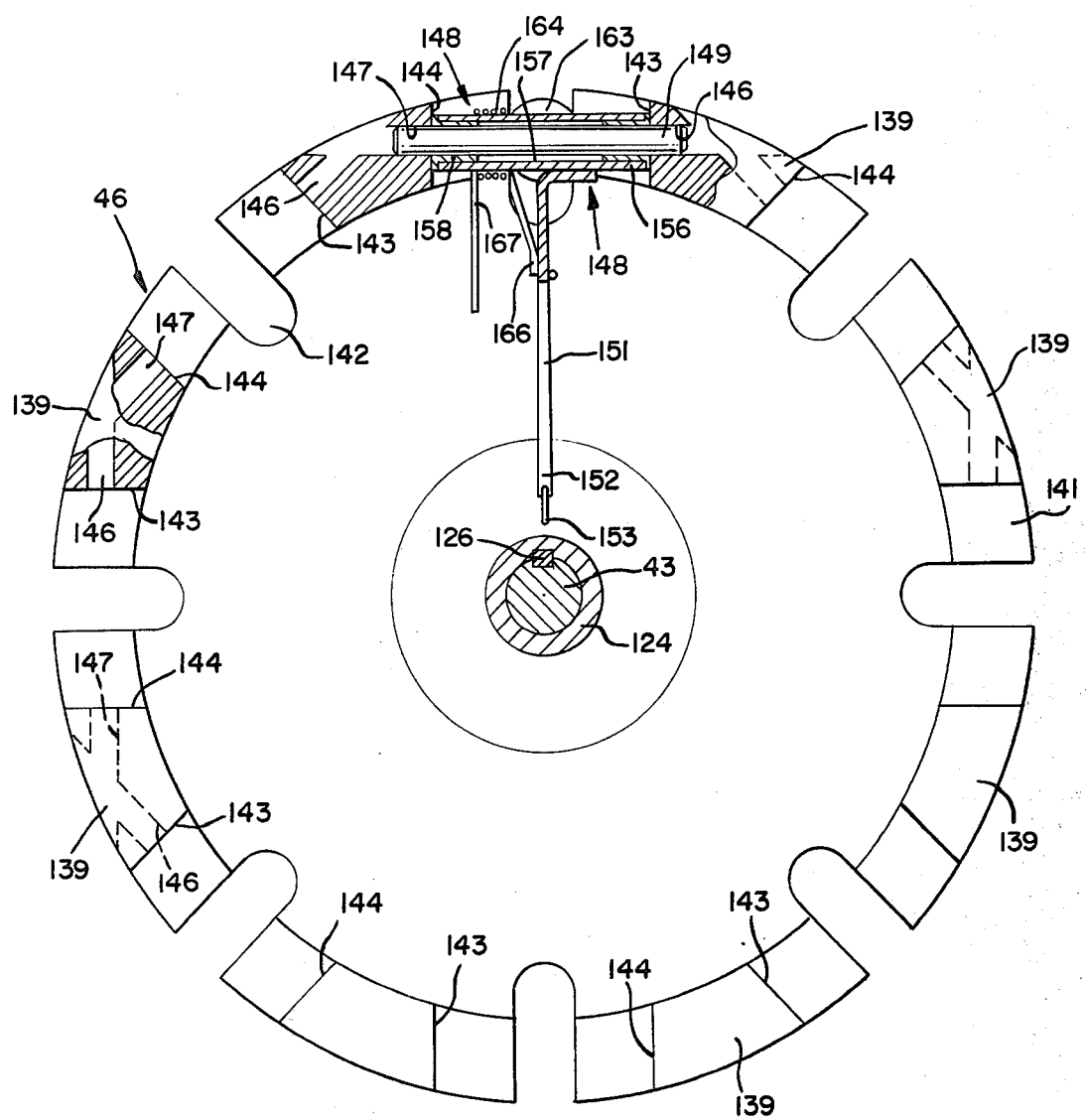
FIG. 14A is a fragmentary vertical sectional view taken in the plane indicated by the line 14A—14A in FIG. 13, and illustrating the inner face of one of the spider wheels with a loop pulling assembly mounted thereon.

Referring to FIG. 7, there is there shown in schematic form the apparatus for producing the elongated chain of interconnected dental floss loops illustrated in FIGS. 1 and 2 or 3. Specifically, the apparatus in its entirety is designated generally by the numeral 41 and includes an appropriate base frame (FIGS. 8, 9 and 10) for supporting the various components as hereinafter described. The apparatus includes a loop forming assembly designated generally by the numeral 42 and which includes a shaft 43 on which are mounted in opposed facing relation and spaced apart on the shaft 43 a pair of spider wheels 44 and 46 as illustrated in FIGS. 13 and 14A. The spider wheels 44 and 46 are appropriately keyed to the shaft and rotate with it, as does an impression or cog wheel 47 which is also keyed to the shaft and rotates with it and with the spider wheels. The impression wheel 47 operates in conjunction with a free-wheeling back-up wheel 48 mounted for free rotation on a shaft 49 and adapted to rotate in unison with the shaft 43 as will hereinafter be explained.

As illustrated schematically in FIG. 7, a first continuous strand 51 of dental floss is fed from a source cone 52 suitably supported on the frame 41, the strand or filament 51 passing through a tensioning device 53, from whence it passes through a guide means (not shown) and partially around the impression wheel 47 in the manner indicated. In like manner, a second strand 54 of dental floss material is fed from a source cone 56, passes through the tensioning device 57 and through a guide means (not shown) and partially around the impression wheel 47 in a path parallel and spaced from the strand 51.

Also adapted to pass between the impression wheel 47 and the back-up wheel 48 with the floss strands 51 and 54 is an elongated strip 58 constituting a pressure sensitive tape preferably fabricated from a synthetic resinous material such as acetate cloth manufactured by Minnesota Mining and Manufacturing Corporation and arranged in such a manner that it feeds from a feed roll 59 suitably journaled on a shaft 61, with the tape strip 58 peeled from the outer periphery of the feed roll 59 and passing over a guide roller assembly designated generally by the numeral 62 and having flanges 63 spaced apart a sufficient distance to provide guiding clearance for the tape strip 58 as it passes between the flanges. The tape edge guide roller 62 is appropriately journaled on a shaft 66.

From the tape edge guide roller 62, the tape 58 passes over and effects rotation of the back-up wheel 48 in such a manner that the adhesive side of the tape faces upwardly toward the impression wheel 47 the spacing between the impression wheel 47 and the back-up wheel 48 being such as to accommodate the thickness of the tape 58 and the strands 51 and 54 of dental floss which pass around the impression wheel 47 after portions of the filaments 51 and 54 have been drawn laterally by the loop puller assembly illustrated in FIGS. 13 and 14A.

After the loops have been drawn laterally, the midportions thereof in contact with the periphery of the impression wheel 47 are impressed on the adhesive side of the pressure sensitive tape 58 and this sub-assembly then, in continuous tape form, and after separation from the impression wheel 47, continues through the apparatus and passes over a tape alignment assembly designated generally by the numeral 67 where the pressure sensitive tape 58 with the dental floss loops adherent thereto are precisely aligned with a second pressure sensitive tape 68 that is appropriately fed from a source roll 69 over an appropriate flanged tape edge guide roll 71 similar to the guide roll 62. The pressure sensitive tape 68 is oriented with respect to the tape 58 so that the adhesive side of the tape 68 faces the adhesive side of the tape 58 so that when the two tapes converge the two adhesive surfaces adhere tightly to one another to form a composite laminate. Such adherence is insured by passing the laminated tapes between pinch rollers 72 and 73 which effectively place sufficient pressure on the two intermediate tapes so as to squeeze the tapes tightly to and around the portions of the floss loops caught therebetween.

The now double thickness composite tape with loops extending transversely therefrom continues on to a perforator wheel designated generally by the numeral 74 which rotates about a shaft 76 and which is provided with cutting elements 77 thereon which cooperate with a back-up roller 78 having two peripheral grooves 78' and 78" to cut in the tape as it passes therethrough the slits 21, 22 and 23 as illustrated in FIG. 1. The tape is not cut in the locations corresponding to the locations of the grooves 78' and 78". Note that the tape is wound partially around the perforator wheel and passes between the perforator wheel and the back-up wheel 78, with the cutting function being effected by the pressure that is exerted between the cutting elements on the perforator wheel and the back-up wheel at their contiguous peripheries. The tape now continues partially wrapped around the back-up wheel 78 and passes freely between the back-up wheel 78 and a cut-off wheel 79 which is provided with a cutting element 80 which provides the transverse cut across the continuous chain or series of loops to provide a predetermined length of such chain, such as a chain encompassing 64 separate yet interconnected loops formed from the dental floss filament. In this respect, the peripheral circumference of the cut-off wheel 79 is proportioned to provide the desired length, the edge of the cutting element 80 pressing against a back-up roller 81 to effect a clean cut of a predetermined length of the completed tape.

It should be understood that in the preferred embodiment of the apparatus and its mode of operation, only the slits 21, 22 and 23 are cut in the tape at this time. Subsequently, cuts in the planes 29, 31, 32 and 33 are made in a separate operation.

From the foregoing, it will be seen that in one continuous process, at a speed of at least 200 feet per minute, two strands of the dental floss material are taken from appropriate sources and threaded through the apparatus in such a way that the loops illustrated in FIGS. 2 and 3 are continuously pulled transversely of the direction in which the filaments and associated tape are traveling at the moment at which the loops are formed, and after formation, the loops are then brought into adhesive contact with the adhesive side of the tape 58 from whence they continue to a second station where a second tape is applied to securely bind the intermediate portions of the loops therebetween. At a third station the different cuts are made in the tape to permit the tape to be separated by the user of the dental floss as it is dispensed from an appropriate spool or container. From this third station, the completed and predetermined length of chain encompassing approximately 64 dental floss loops are appropriately processed to cure the adhesive binding the loops together so as to increase the strength of retention of the filament end portions adhesively caught between the tabs 12 and 13 as illustrated in FIG. 1. This process may involve heating the continuous tapes for a period and at a temperature sufficient to provide a structure that will withstand a tensile force of from about six pounds to more than fifteen pounds. Following processing to cure the adhesive, which may be effected at room temperature over a longer interval, the continuous chains of predetermined length are appropriately cut in the planes 29, 31, 32 and 33 and wound on a spool for packaging and distribution.

Figure 8:
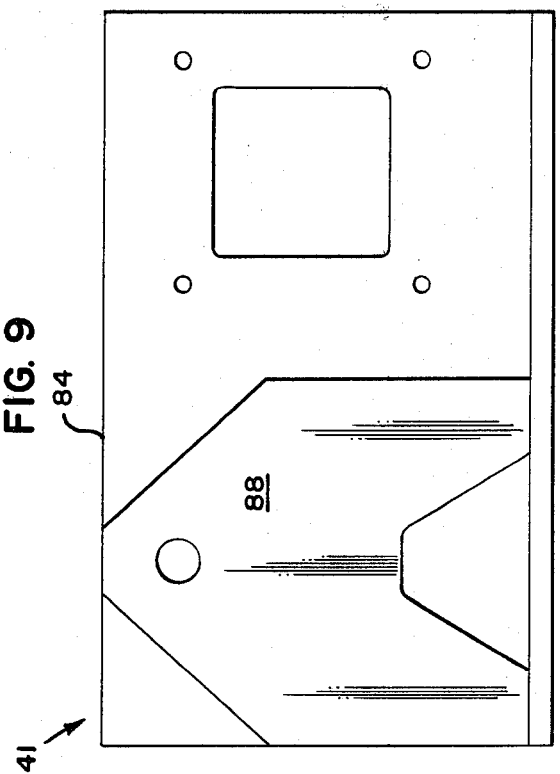
FIG. 8 is a front elevational view of the base frame shown apart from the remainder of the apparatus.
Figure 9:
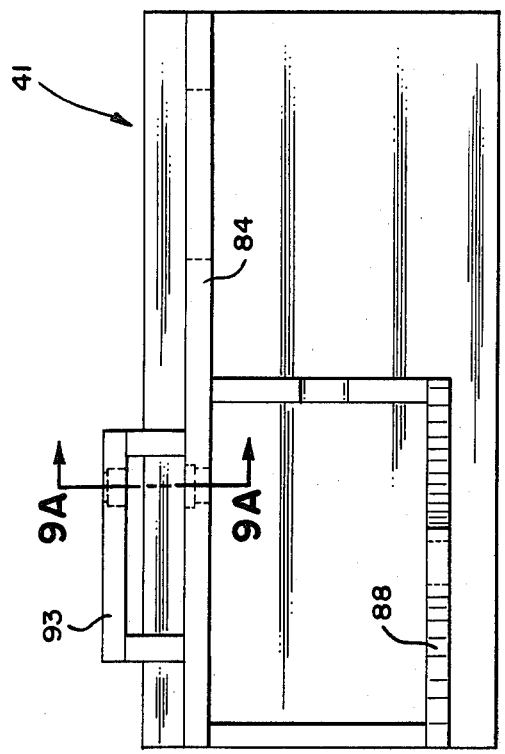
FIG. 9 is a top plan view of the base frame shown apart from the remainder of the apparatus.
Figure 9A:
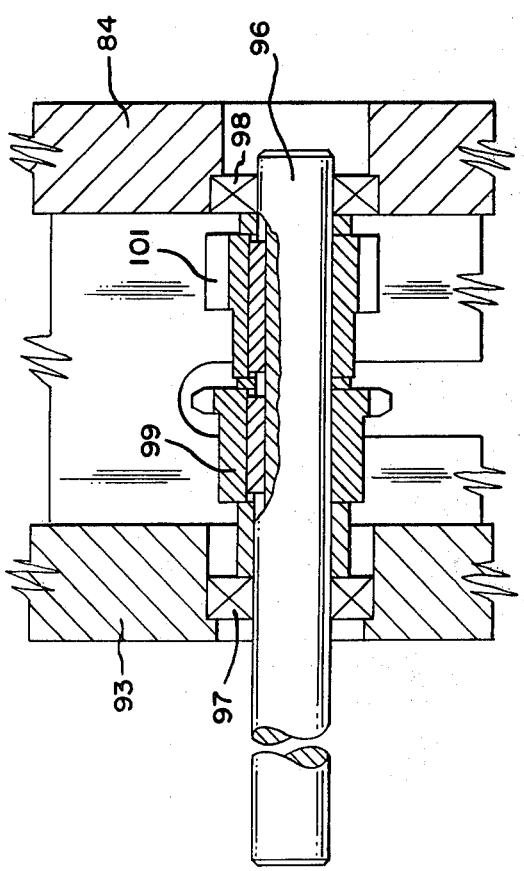
FIG. 9A is an enlarged fragmentary sectional view taken in the plane indicated by the line 9A—9A of FIG. 9, and having added thereto the main drive shaft for the apparatus.
Figure 10:
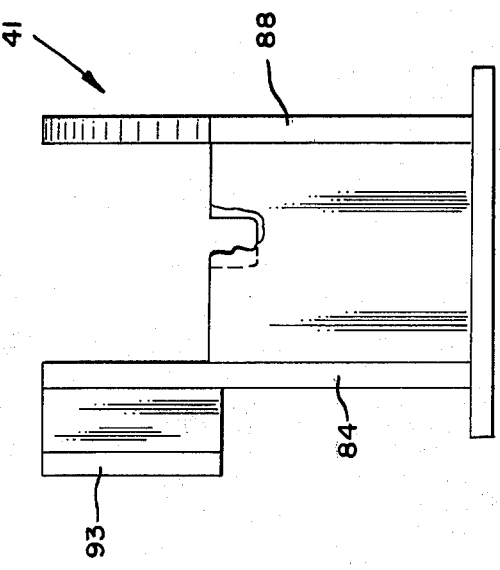
FIG. 10 is an end elevational view of the base frame shown apart from the remainder of the apparatus.

In terms of detailed structure, the apparatus for producing the continuous chain of dental floss loops in the forms illustrated in FIGS. 1 and 3 comprises a base frame structure illustrated in FIGS. 8, 9 and 10 and shown there devoid of any other apparatus in the interest of clarity. The base frame is designated generally by the numeral 81, is fabricated conveniently from metal plate, and includes a base plate 82 rectangular in configuration as illustrated and adapted to be supported on any appropriate supporting structure such as a support frame or table (not shown). Mounted perpendicularly on the base plate and adjacent its rear edge 83 is a rear mounting plate 84 which is joined at one end by a transversely extending end plate 86 shorter in height than the rear mounting plate and generally rectangular in configuration. Spaced from the end plate 86 is a second end plate 87 which is also perpendicular to the base plate 82 and with the rear plate 86 projects toward the forward edge 87 of the base plate, where the forward edges of the end plates 86 and 87 are joined by a front mounting plate 88 mounted perpendicularly on the base plate 82 and extending to the same height as the rear mounting plate. The rear mounting plate, the end plates, and the front mounting plate are all suitably secured together by appropriate means, such as screws (not shown) so that an exceptionally rigid and vibration-free composite base frame is formed.

Mounted on the rear mounting plate and extending therefrom in a direction opposite to the end plates 86 and 87 is a drive housing designated generally by the numeral 89 and including end support plates 91 and 92 and a bearing plate 93 fixed to the end support plates 91 and 92 and cooperating with the rear mounting plate to form journals for a drive shaft assembly designated generally by the numeral 94. As illustrated, the drive shaft assembly includes a shaft 96 rotatably supported between the rear mounting plate 84 and the bearing plate 93 by the interposition therebetween of appropriate bearing assemblies 97 and 98 as shown. Mounted on the shaft 96 and keyed thereto for rotation therewith is a drive sprocket 99 and a drive gear 101. Appropriate spacers are provided on the shaft to maintain the axial position of the sprocket and gear on the shaft and maintain their alignment with other drive elements as will hereinafter be explained.

As explained in connection with the description of the schematic illustration of FIG. 7, and referring now to FIG. 11, the tape feed roll 59 constitutes an indeterminant length of pressure sensitive tape wound on the outer periphery of a hub or spool 102 which is journaled on a pivot pin 61 mounted adjacent the free end of a pivot arm 103 which is itself pivotally mounted on a rear mounting bracket 84' by a pivot pin 104. It is important to note that the mounting of the feed roll 59 on the pivot arms 103 in relation to the pivot 104 is such that gravity tends to pivot the assembly counterclockwise as illustrated in FIG. 11 so that the outer periphery 106 of the feed roll 59 bears continuously against the inner periphery 107 of the guide roller assembly 62. Additionally, it should be noted that a peripheral portion of the feed roll 59 next adjacent the outer periphery 106 lies between the parallel flanges 63 of the guide roller, thus insuring proper alignment of the pressure sensitive tape 58 as it leaves the guide roller 62.

From the guide roller 62, the strip 58 of pressure sensitive tape passes into the loop forming assembly designated generally by the numeral 42 and between the spider wheels 44 and 46 illustrated in structural detail in FIGS. 13 and 14A sufficiently to explain their structure and function. Within the loop forming assembly the tape passes between the impression wheel 47 and the free-wheeling back-up wheel 48, the latter being journaled for rotation on a shaft 49 by means of bearings 108 and 109 interposed between the hub 112 and the shaft 49. Appropriate collars 113 and 114 retain the back-up wheel 48 in lateral alignment with the impression wheel 47 as illustrated in FIG. 13. Precise positioning of the back-up wheel 48 is provided by an adjusting assembly designated generally by the numeral 116 associated with each end of the shaft and adapted to mount the shaft between the inner surfaces of the rear mounting plate 84 and front mounting plate 88. The adjusting assembly 116 includes a shaft mounting block 117 associated with each end of the shaft, an adjusting block 118 mounted on the associated mounting plate as shown, and an adjusting screw 119 adjustable in relation to the adjusting block 118 to adjust the position of each end of the shaft.

Referring to FIG. 13, it will be seen that the two spider wheels 44 and 46 are mounted adjacent opposite ends of the shaft 43 and adjacent the associated rear and front mounting plates 84 and 88, respectively. In the interest of brevity in this description, since both of the spider wheels are essentially identical, only one will be described in detail. Both spider wheels 44 and 46 are mounted for rotation with shaft 43 which is in turn journaled for rotation in bearings 121 and 122 mounted appropriately in bores formed in mounting plates 84 and 88, respectively. The inner races of the bearings are press fitted on the shaft, and the shaft is precluded from axial displacement once mounted on the plates by a snap ring 123.

As illustrated in FIG. 13, the impression or cog wheel 47 is mounted centrally between the two spider wheels 44 and 46, which are mounted on opposite sides thereof, each of the spider wheels including a hub portion 124 secured to the shaft by an appropriate key 126 which also secures for rotation with the shaft a retainer ring 127 which is provided with a circumferential series of sixteen bores that extend longitudinally through the retainer ring and each of which receives one end portion of a spring wire 128 while the other end of the spring wire projects through the rim of the impression wheel 47 as illustrated to provide a projecting end portion or cog 129 which functions in a manner which will hereinafter be explained.

As illustrated in FIG. 13, the impression wheel adjacent its outer periphery is provided with a generally T-shaped cross-section, with each flange of the T-shaped rim of the impression wheel being provided with a circumferential series of bores 131 equal in number to the bores formed in the retainer ring 128 and which slidably receive the associated end portion 129 of each of the wires 128. The projecting end portion 129 of each of the wires projects beyond the outer peripheral surface 132 of the impression wheel approximately 1/16 of an inch and the wire 128 is preferably fabricated from 18 gauge piano wire so that it possesses considerable resilience in its length between the retainer ring 127 and the impression wheel 47.

Referring to FIG. 13, the retainer ring 127' on the left side of the impression wheel 47 is also provided with a circumferential series of bores that receive the ends of resilient wires 128'. Thus, since the impression wheel 47 is secured to the shaft 43 by key 133, when the shaft 43 is rotated by meshing of drive gear 101 with driven gear 134 secured to the shaft 143 by taper pin 136, both spider wheels 44 and 46, together with the retainer rings 127 and 127' and the centrally disposed impression wheel 47 will rotate in unison about the longitudinal axis of the shaft 43.

Each of the spider wheels 44 and 46 includes a web portion 137 that extends radially outwardly and generally conically from the hub 124 which is located generally at the apex of the conical web 137. Adjacent its outer circumferential peripheral portion 138, the generally conical web 137 is provided with a plurality of axially extending bearing blocks 139, there being eight in number of these axially projecting bearing blocks, each being integral with the outer peripheral portion of the web. The eight bearing blocks 139 are equally spaced about the periphery of the spider wheel and separated from each other by circumferentially equally spaced web portions 141 each of which web portions is provided with a radially inwardly extending slot 142 disposed centrally and symmetrically between the associated bearing blocks 139 on opposite sides thereof.

Referring to FIG. 14(A), the opposed surfaces 143 and 144 of opposed bearing blocks 139 are parallel to each other and spaced an equal distance on opposite sides of a plane passing through the axis of rotation of the spider wheel and medianly of the associated slot 142. Formed in each of the faces 143 and 144 of the bearing blocks 139 are bores 146 and 147, respectively. Each of the bores 146 and 147 are oriented with respect to the associated face 143 and 144, respectively, so that the axis of each bore is perpendicular to the associated face 143 and 144. Thus, as illustrated in FIGS. 14 and 14(A), adjacent bearing blocks 139 and the bores 146 and 147 disposed therein on opposite sides of the slots 142 serve to pivotally mount a loop puller sub-assembly designated generally by the numeral 148 and including a shaft 149 opposite end portions of which are journaled in the bores 146 and 147, while the intermediate portion of each shaft is utilized to pivotally support a cantilever arm 151 which extends radially inwardly toward the central axis of the spider wheel and which on its inner end portion 152 is provided with a hook member 153 which terminates in a re-entrant portion 154 as shown.

As illustrated in FIGS. 13 and 14(A), the loop puller sub-assembly 148 includes a body portion 156, generally rectangular in its configuration and provided with a central bore 157 the ends of which receive bushings 158 which in turn rotatably receive the shaft 149. Mounted on one flat side of the central body portion 156 is a depending cantilever arm 151 suitably secured to the central body portion as by screws (not shown). Extending from one edge of the central body portion is a cylindrical projection 159 co-axial with the axis of the bore 157. Projecting from an adjacent edge of the central body portion is a cylindrical stud 161 the end of which is reduced in diameter as shown at 162 to receive a cam follower 163 rotatably mounted thereon.

Also mounted on the loop puller sub-assembly 148, specifically on the cylindrical projection 159 thereon, is a coil spring 164 one end 166 of which engages the cantilever arm 151 as shown, while the opposite end 167 impinges against the associated spider wheel. The relationship between the spider wheel on which the loop puller sub-assembly 148 is mounted and the spring 164 is such that the cantilever arm 151 is resiliently biased so as to swing the cantilever arm away from the spider wheel. Stated another way, the spring 164 biases the cantilever arm 151 in a manner to urge the hook 153 toward the impression wheel 47.

Figure 21:
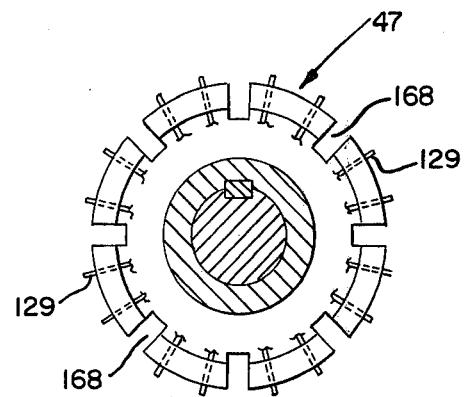
FIG. 21 is a side elevational view of the impression or cog wheel taken in the direction of the arrows 21—21 in FIG. 20.

It is important to note that while I have illustrated in FIGS. 13 and 14(A) only one of the loop puller sub-assemblies on each of the spider wheels, there are actually eight such sub-assemblies on each of the spider wheels, with eight cantilever arms 151 and eight hook structures 153, each being resiliently biased toward the impression wheel 47 by an associated spring 148. It is also important to note that as illustrated in FIG. 21, there are only eight slots 168 equally spaced around the periphery of the impression wheel 47 and that obviously, all of the hooks 153 of each spider wheel cannot simultaneously engage the respective slots with which they are aligned. Accordingly, means are provided to control the pivotal action of the cantilever arms 151 of each loop puller sub-assembly 148 on each spider wheel in cooperation with the movement of the cantilever arms 151 of the loop puller sub-assembly 148 mounted on the opposite spider wheel in a manner which will now be explained.

To control actuation of the eight loop puller sub-assemblies 148 mounted on each spider wheel, there is associated with each of the spider wheels a cam that works in conjunction with the cam follower 163. With respect to the spider wheel 44, shown on the left in FIG. 13, there is provided a cam 171 shown in cross-section in FIG. 13 and shown in full elevation in FIG. 15. As shown in these views, the cam 171 is provided with the central body portion 172 provided with four tapped bores 173 spaced equidistant from the central axis 174 which is coincident with the central axis of the shaft 43 with which the spider wheels rotate, the bores 173 being utilized with appropriate cap screws 176 to secure the cam rigidly to the associated rear mounting plate 84 as shown. The cam 171 is provided with a rim portion 177 the outer peripheral surface 178 of which is configured with respect to the central axis 174 to provide the requisite pivotal reciprocation of the cantilever arms 151 as the spider wheel 44 is rotated and each of the eight cam followers 163 successively follow the contour of the peripheral surface 178 of the cam.

Figure 15:
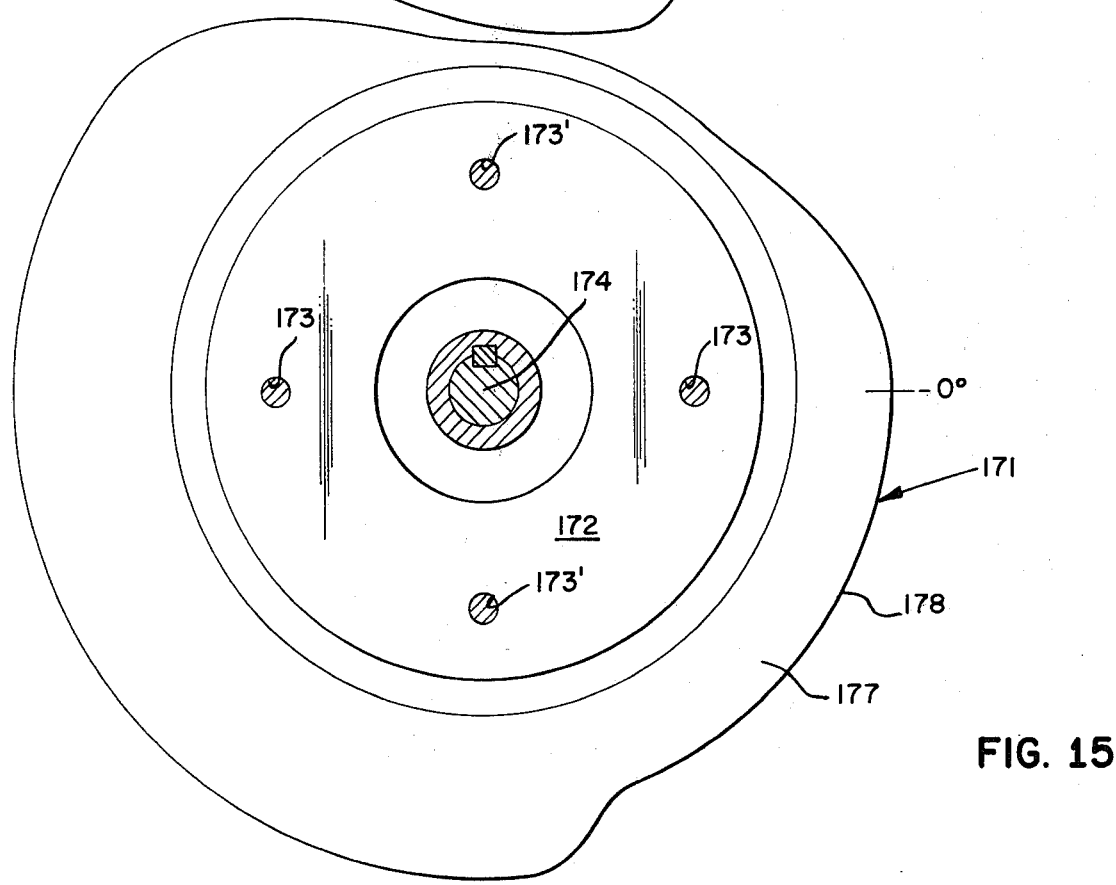
FIG. 15 is a fragmentary vertical sectional view taken in the plane indicated by the line 15—15 in FIG. 13, and illustrating the configuration and 90° offset orientation of the left cam in relation to the right cam.

In this respect, it is noted that the cam surface 178 encompasses a full 360° about the central axis 174. As illustrated in FIG. 15, with the bores 173 arranged horizontally, the zero degree point on the cam face 178 lies in a plane which includes the central axis of the cam and the axes of the bores 173. Measured counterclockwise about the central axis 174 of the cam, it will be noted that the cam face 178 descends toward the central axis commencing at the 0° point and extending to the 50° point measured from the 0° point. From the 50° point to the 90° point, i.e., for 40° of arc, the cam surface 178 possesses a constant relatively short radius from the central axis 174. At the 90° point the radius of the cam surface commences to increase until it reaches a maximum at the 140° point of arc measured from the 0° point. Thus, the 40° of arc which are at the least distance from the central axis 174 constitutes the low point of the cam and constitutes the cam surface which when engaged by the cam follower 163, permits the biasing force of the loop puller assembly 148 to pivot the cantilever arm 151 toward the impression wheel 47, with the hook structure 153 reaching its innermost position during this 40° interval on the surface of the cam. Note also that between the 140° point on the cam surface 178 to the 277° point thereon, the cam surface 178 possesses a constant radius which is maximum in its extent for this cam, and then through a 13° arc between 277° and 290°, the radius drops somewhat to provide a smaller arc between 290° and 0°.

In like manner, referring again to FIG. 13, it will be noted that with respect to the right side of the figure, adjacent the front mounting plate 88, there is provided a second cam 181 having two pairs of bores 182 and 182' equally spaced circumferentially about the central axis 183 which is coincident with the central axis 174 of the cam 172 and the axis of shaft 43. The cam 181 is provided with a rim portion 184 having a cam face 186 which extends 360° about the central axis 183. With respect to the cam 181, it may be assumed that the zero degrees point on the cam surface 186 lies in a plane which also includes the axes of bores 182, shown to be in vertical alignment in FIG. 14. From the zero degrees point on cam face 186, and measured counterclockwise between the zero degree point and the 140° point, the contour of the cam face 186 is identical to the contour of the cam face 178 on cam 172. With respect to cam 181, between the 140° point and 187°, i.e., for an arc of 47°, the cam face 186 possesses a maximum radius and then through a thirteen degree arc, blends to a smaller radius between 200° and the zero degree mark as shown.

Obviously, the cam 171 is associated with the spider wheel 44, while the cam 181 is associated with the spider wheel 46. Thus, each cam controls the reciprocating or pivotal movement of each of the eight loop puller sub-assemblies mounted on the associated spider wheel. Because there are only eight slots in the periphery of the impression wheel 47, and there are a total of sixteen loop puller sub-assemblies 148 on both spider wheels, it is apparent that engagement of the hook structure 153 in the slots formed in the impression wheel 47, must alternate from one spider wheel assembly to the other as rotation progresses about the cam faces 178 and 186. To accomplish this, the two cams 171 and 181 are mounted on their associated mounting plates 84 and 88 so that the zero degree points, and thus the cam surfaces possessing the least radius, are positioned 90° offset from one another.

Thus, in the structure illustrated, the left or rear cam 171 attached to the rear mounting plate 84 is mounted so that the zero degree point of cam surface 178 is in planar alignment with horizontally aligned bores 173, so that the ninety degree point on the cam surface 178, measured counter-clockwise from the zero degree point, is associated with the upper edge of the rear mounting plate 84. By contrast, the right or front cam 181 is mounted on the front mounting plate 88 so that the zero degree point of the cam surface 186 is in planar alignment with the bores 182 and lies in a vertical plane so that the zero degree point on the cam face 186 lies next adjacent the top edge of the front mounting plate 88 and the 90° point on the cam surface 186 lies aligned in planar alignment with the bores 182' which lie in a horizontal plane. Thus, the functional result of such 90° offset of the two cams 172 and 181 is that at any given moment there will be no more than one hook structure 153 from each of the spider wheels engaging a slot in the impression wheel 47 while the other seven of each assembly will be either moving toward or moving away from the impression wheel due to the configuration of the remaining portion of each associated cam.

Figure 22:
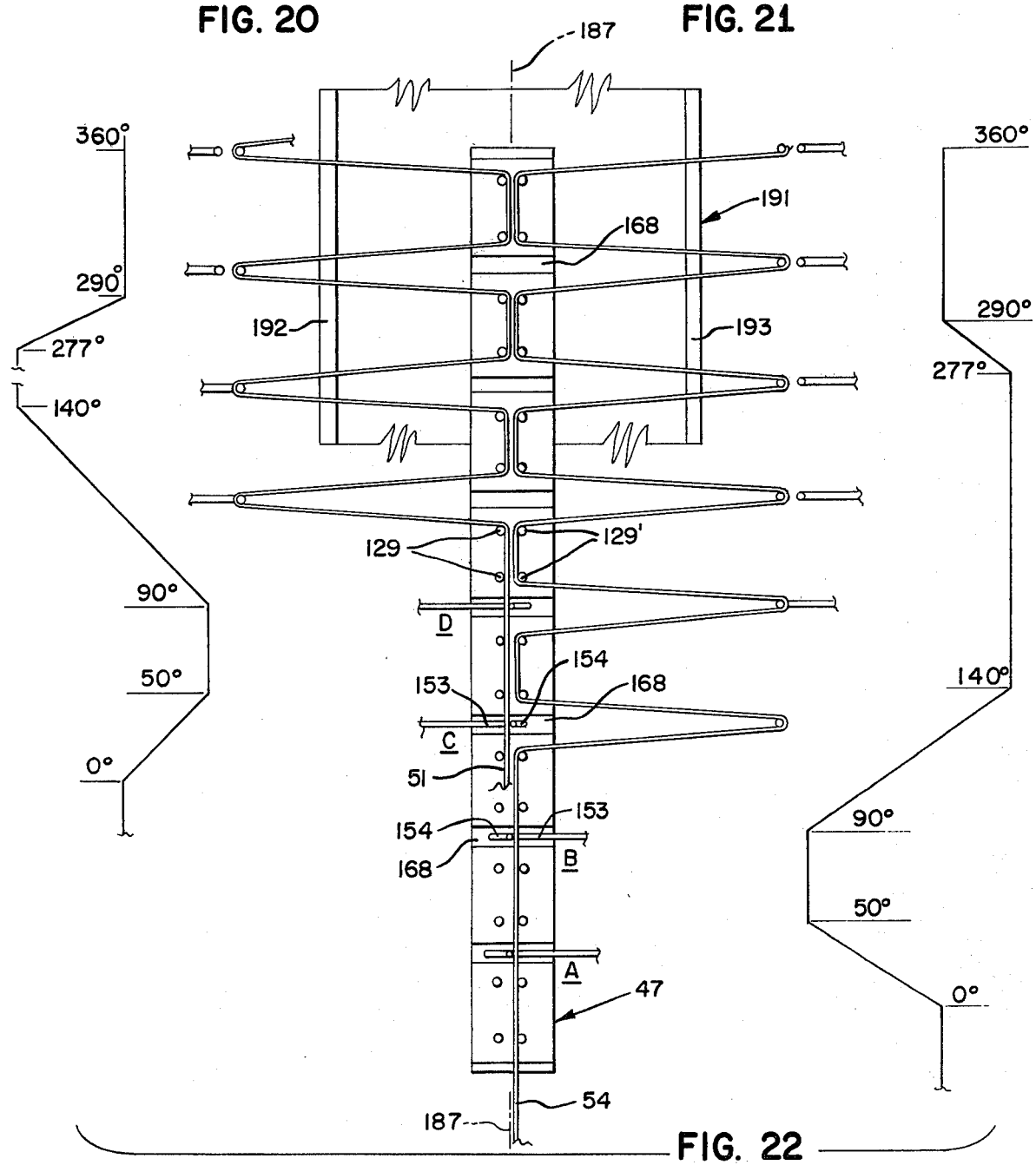
FIG. 22 is a schematic view illustrating the surface of the impression or cog wheel in developed form, together with the profiles of the left and right cams, and showing the intervals during which the loop-pulling assemblies are active and inactive.

Referring specifically to the action of the loop puller assemblies associated with the spider wheels 44 and 46, reference is made to FIG. 22 which represents schematically the action of the impression wheel 47 and its cooperative relationship with each set of loop puller assemblies mounted on the spider wheels 44 and 46. Thus, considering that the surface of the impression wheel 47 is illustrated in its developed form, the eight slots 168 are shown equally spaced along the surface representing the surface of the impression wheel with the cogs 129 projecting therethrough as shown, there being four cogs projecting from the surface of the impression wheel 47 between each pair of slots 168. The four cogs are arranged in pairs on opposite sides of a central plane designated by the line 187.

To facilitate an explanation of the manner in which the impression wheel 47 cooperates with the pivotally mounted and reciprocating cantilever arms or fingers 151, the pairs of cogs to the left of the reference line 187 are designated 129, while the pairs of cogs on the right hand side of the reference plane 187 are designated 129'. It will be seen from FIGS. 7, 13 and 22 that as the filaments 51 and 54 of dental floss are imposed on the impression wheel 47 from their respective sources, the two filaments 51 and 54 lie juxtaposed in spaced parallel relationship between the pairs of cogs 129 and 129', the filament of dental floss 51 lying next adjacent the cogs 129, while the filament 54 of dental floss lies next adjacent the pairs of cogs 129'. Thus, in response to rotation of the shaft 43 by engagement of the gear 134 with the gear 101 of drive shaft 96, the filaments 51 and 54 are partially wound about the impression wheel 47 and the loop pulling assemblies, including the spider wheels, move about the peripheral cam surfaces of cams 171 and 181 in such a way that the hook structures on the ends of cantilever arms 151 move inwardly at timed intervals depending upon the position of the cam follower on the cam surface so that at a predetermined point in time the hook structure 153 enters a slot 168 and positions itself so that the re-entrant portion 154 lies behind the dental floss filament 54 as shown at the bottom of FIG. 22.

Rotation of the assembly through 45° places the hook structure 153 at a position where it is about to retract as indicated by the cam profile on the right in FIG. 22, and continued movement then causes the hook structure 153 to move to the right as illustrated in FIG. 22, the re-entrant portion 154 hooking the filament 54 and pulling it to form a "shed" the height of which is determined by the extent of retraction of the hook structure 153 as controlled by the contour of the cam. Because of the offset positions of the cams 171 and 181, at the moment that the hook structure 153 pulls a shed on filament 51, on the opposite side of the impression wheel, the corresponding hook structure 153 mounted on the opposite spider wheel, penetrates the same slot from which the opposite hook structure has been retracted and the hook structure engages behind the filament 51 positioned next adjacent the pairs of cogs 129.

It will be noted by comparing the position of the hook structure 153 mounted on the left side of the impression wheel as viewed in FIG. 13 with the cam profile shown to the left in FIG. 22, that the cam follower has reached the cam surface of least radius, thus placing the hook structure at its innermost impression wheel penetrating position. Continued rotation through 45° from station C to station D does not alter the position of the hook structure 153 within the associated slot formed in the impression wheel. However, upon reaching station D, the cam follower now starts to climb in its transition from the minimum radius portion of the cam surface to the next highest elevation thereof as illustrated by the cam profile, with the result that the hook structure 153 and the re-entrant portion 154 hooked behind the filament 51 moves to the left and pulls the filament 51 with it, causing it to form a shed as illustrated, which lies opposite the shed formed on the opposite side of the impression wheel.

These opposed positions of the filament sheds are retained by their respective hook portions 153 until the impression wheel 47 has rotated sufficiently that the periphery thereof comes in contact with the adhesive surface of the pressure sensitive tape 58, resulting in the mid sections of the filaments which are pulled around the cog pairs 129 and 129' to be impressed onto the adhesive surface of the pressure sensitive tape 58 and to be retained thereon. As the impression wheel 47 continues to rotate and presses the tap against the surface of the back-up wheel 48, the cogs 129 are resiliently depressed or retracted inwardly toward the surface of the impression wheel, thus releasing the filaments that have theretofore been engaged by the pairs of cogs, permitting the single layer of pressure sensitive tape 58 with the opposed filament sheds now formed thereon to continue through the apparatus for further processing as will now be explained.

As the single layer of pressure sensitive tape 58 leaves the impression wheel 47, with the laterally and oppositely extending sheds formed from continuous filaments of dental floss attached thereto, in the form of two opposed series of successive loops, i.e., considering each shed as a loop, the tape with the laterally extending sheds of dental floss passes downwardly into a channel designated generally by the numeral 191 (FIG. 22), the channel including upright flanges 192 and 193 over which the laterally extending sheds of dental floss must pass as they leave the impression wheel 47. The height and positioning in terms of lateral spacing from the central plane 187 of the flanges 192 and 193 is such that when the cam follower 163 encounters the sharp transition point on each of the cams and indicated on the left cam by the numeral 194 and indicated on the right cam by the numeral 196, the hook structure 153 is given a downward and laterally inward translation that releases the bight of the associated shed. Substantially simultaneously, the sheds pass over the top edges of the flanges 192 and 193 which causes the ends of the sheds to be deflected upwardly as the tape progresses further and further from the impression wheel 47. This results in the sheds clearing all of the remaining hook structures and permits the sheds, which might otherwise hook on projecting structures, to pass uninterrupted through the apparatus.

From the impression wheel 47, the tape with the sheds attached to it and extending laterally therefrom, passes to the alignment assembly 67 which includes, as indicated in FIG. 16, a pair of centering rollers 196 and 197 freely rotatable on stub shaft 198 and 199 which are arranged about horizontal axes that are angularly disposed one with the other so that the associated and mutually facing sides of the centering rollers 196 and 197 converge toward each other in the direction in which the tape 58 is moving. It is important to note that the peripheral surfaces 201 and 202 of the centering rollers 196 and 197, respectively, are generally conical in their configuration or slightly tapered as shown. The effect of causing the tape 58 to pass over these tapered peripheral surfaces is to cause the tape to be exactly centered by the two rollers and to resist the tendency of the tape to be displaced laterally one way or the other. Accordingly as the tape 58 with attendant floss sheds thereon passes over the centering rollers 196 and 197, it is in the proper position to have applied thereon a second strip of pressure sensitive tape 68 as illustrated in FIG. 7.

The second or upper most layer of pressure sensitive tape 68 is provided with an adhesive layer on its underside so that when the pressure sensitive tape 68 comes in contact with the pressure sensitive tape 58, the two adhesive surfaces are brought into engagement in perfect alignment and are pressed together by the pinch rollers 72 and 73.

Figure 17:
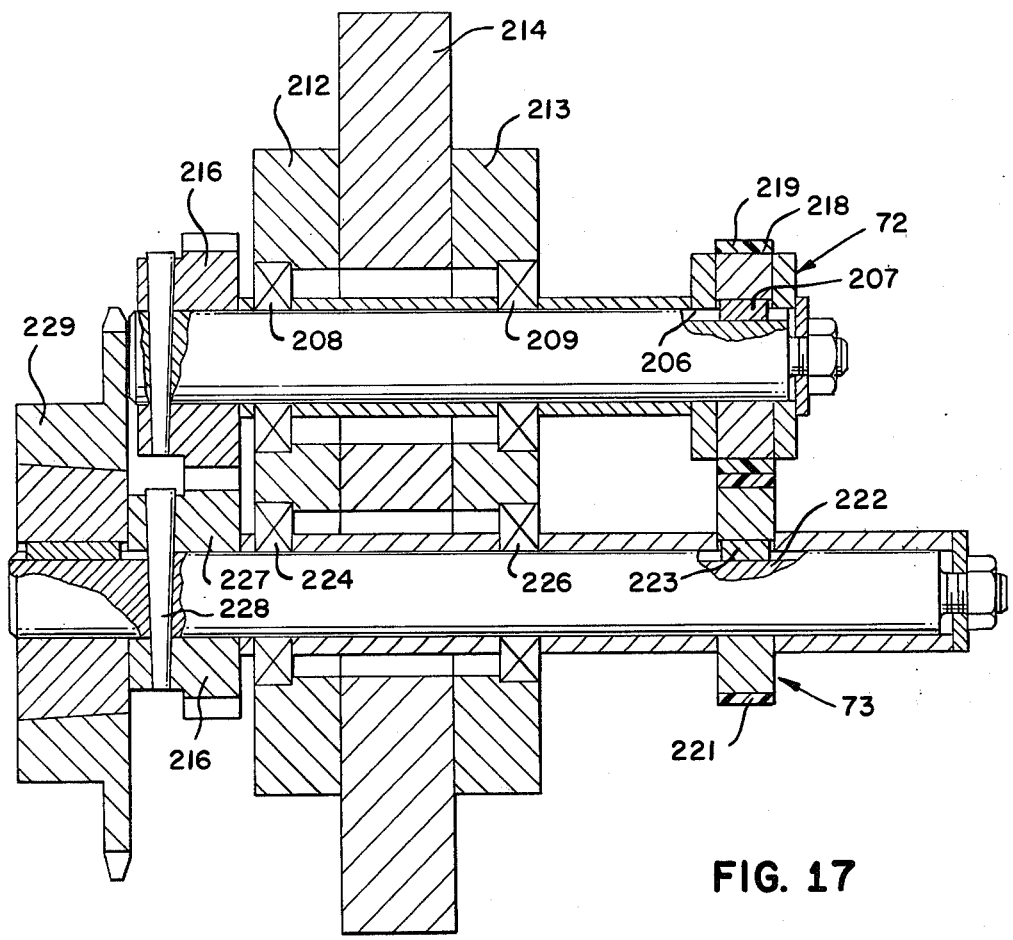
FIG. 17 is a fragmentary vertical cross-sectional view taken in the plane indicated by the line 17—17 in FIG. 7, and illustrating the pinch roller assemblies that press the two pressure sensitive tapes together to form a single composite tape.

The pinch roller assembly is shown in structural detail in FIG. 17 where it is seen that the pinch roller 72 is mounted for rotation with a shaft 206, secured thereto by a key 207, with the shaft being journaled for rotation on the rear mounting plate 84 through appropriate bearings 208 and 209 suitably supported on plates 212 and 213 apertured to receive the shaft and which plates are in turn secured to a center plate 214 that is fastened to the rear mounting plate 84. The shaft 206 is provided with a gear 216 as shown which is driven in a manner which will hereinafter be explained. The pinch roller 72 is provided with a resilient rim 219 which cooperates with a complimentary resilient rim 221 mounted on the pinch rollers 73 as shown. The pinch roller 73 is mounted on a shaft 222 by means of an appropriate key 223 and is also supported by appropriate bearings 224 and 226 on the plate assembly 212-214 so that the shaft 222 extends through the rear mounting wall 84 where it is provided with a gear 227 that is secured to the shaft by a taper pin 228. The shaft 222 is driven by a sprocket 229 which is connected by an appropriate chain to the motor drive sprocket 99 illustrated in FIG. 10.

Figure 18:
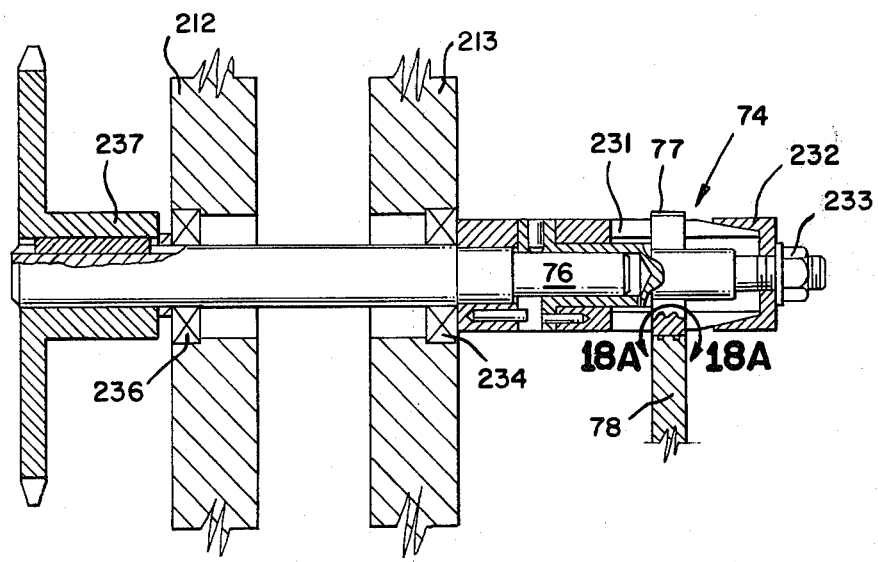
FIG. 18 is a fragmentary vertical cross-sectional view of the perforater or tape-slitting roller assemblies, taken in the plane indicated by the line 18—18 in FIG. 7.
Figure 20:
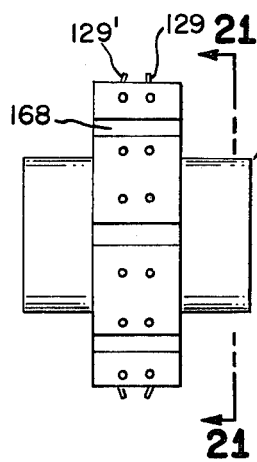
FIG. 20 is a top plan view of the impression or cog wheel taken in the direction indicated by the arrows 20—20 in FIG. 13.

After the now composite or laminated tape leaves the pinch roller assembly 73 it passes onto the perforator wheel designated generally by the numeral 74 and described in conjunction with FIG. 7. The detailed structural aspects of the peforator wheel 74 are illustrated in FIG. 18 where it is seen that an appropriate number of the cutting elements 77 are retained in cutting position spaced circumferentially about a slotted collet 231, the cutting elements being frictionally bound in appropriate slots of the collect by radially inwardly directed pressure imposed by a tapered cup member 232 when the nut 233 is tightened. Shaft 76 is appropriately journaled in the frame by bearing members 234 and 236. Rotation of the shaft 76 is synchronized by chain drive from the main drive shaft 96 and sprocket 99 to the sprocket 237. The backup roller 81 associated with the cutoff wheel 79 is appropriately journaled on a stub shaft (not shown) mounted on the frame and projecting therefrom so as to position the backup wheel or roller 81 in a plane coincident with the plane of the cutoff wheel 71.

As previously discussed, the now completed tape is cut to a predetermined length by the cutoff wheel 79, that length being approximately 50.26 inches and containing 64 of the completed loops as illustrated in FIGS. 1, 2 and 3. The predetermined length of tape is now preferably subjected to the heat processing previously discussed in order to "age" or cure the product in a relatively short interval. Alternatively, the tapes may be stored for a longer interval at room temperature so as to effect natural curing or aging of the laminated tapes so as to increase the retentiveness of the laminated tapes for the floss filaments trapped or caught therebetween, thus increasing the tensil force that must be imposed on the floss strands or filaments to effect detachment thereof from the tapes. Such force is obviously much more than the force that is normally applied on the filament during the flossing process.

Having thus described the invention, what is believed to be new and novel and sought to be protected by Letters Patent of the United States is as follows:

I claim:

1. As an article of manufacture, an elongated chain of indeterminate length and including a tape portion and a dental floss portion;

(a) said tape portion having adhesive on one surface thereof; and (b) said dental floss portion having sections thereof intermediate its ends adhesively attached to said tape portion.

2. The combination according to claim 1, in which said tape portion comprises a pair of juxtaposed tapes adhesively bonded together to form a laminate, and said floss portion includes predetermined portions caught between said two layers of tape.

3. The combination according to claim 1, in which said tape portion constitutes a continuous strip of tape of indeterminate length, said floss portion comprises a first strand of dental floss arranged with respect to one longitudinal edge of such tape to provide a multiplicity of successive loops of such floss along the associated longitudinal edge of the tape, a portion of said floss filament between each of the loops being adherent to the surface of said tape;

(a) said floss portion including a second filament of dental floss arranged with respect to the opposite longitudinal edge of said tape to provide a multiplicity of loops therealong positioned in transverse opposition to the loops formed on the opposite side of the tape, portions of said second filament of dental floss being adherent to the surface of said tape; and (b) slit means formed in said tape to devine a weakened section therein that may be parted from an adjacent section thereof by appropriate tensile stress applied to said weakened section, said first and second dental floss filaments in the portion thereof adherent to the surface of said tape, being severed whereby when said tape sections are parted a predetermined length of said tape in the form of a tab remains attached to associated severed ends of said opposed loops.

4. As an article of manufacture, a continuous chain formed from interconnected loops of dental floss material, each of said loops being formed from a pair of juxtaposed lengths of dental floss material opposite and associated ends of which are interconnected by an adhesive tab whereby separate yet interconnected dental floss loops are formed in an elongated chain, and means formed in each of said tabs associated with adjacent dental floss loops whereby one dental floss loop may be disengaged from an associated dental floss loop by imposition of a predetermined amount of tensile force thereon.

5. In apparatus for the production of a continuous chain of indeterminate length formed from a multiplicity of interconnected loops of dental floss material, associated dental floss loops being interconnected one with the other by an adhesive tape member to which associated ends of the dental floss material is adherent, the combination comprising:

(a) first and second independent sources of dental floss material in filament form and of indeterminate lengths from which a pair of dental floss filaments may be withdrawn;

(b) means including a rotatable member upon which said pair of dental floss filaments may be disposed continuously in spaced parallel juxtaposition as said pair of dental floss filaments are withdrawn from said first and second sources;

(c) means associated with said rotatable member adapted to periodically engage said strands of dental floss filament material and draw it in a direction transverse to the direction of rotation of said rotary member whereby a shed or loop of said dental floss material is formed on opposite sides of said rotary member;

(d) means for imposing and adhesively adhering to said pair of dental floss filaments on the portion thereof engaged by said rotary member a first adhesive tape member to cause said filament loops to be adhesively secured to said first tape member in successive fashion;

(e) means for imposing on said first tape member a second tape member whereby portions of said dental floss filament loops lie caught between said first and second tape members when said first and second tape members are laminated one to the other; and (f) means for perforating said first and second tape members at predetermined intervals whereby sections of said tape are defined by transverse extending slits forming weakened sections along said laminated tape members, said weakened sections being disposed between associated loops of said dental floss material whereby one such loop may be separated from the next adjacent loop by imposing a predetermined tensile force on said weakened section of said laminated tape.

6. The combination according to claim 5, in which said pair of dental floss filaments are pulled from their respective sources under constant tension.

7. The combination according to claim 5, in which said rotary member that receives said pair of dental floss filaments in spaced parallel juxtaposition constitutes a cog wheel, said cog wheel having a multiplicity of depressible cogs projecting through the periphery thereof in two circumferential series, said pair of spaced parallel strands of dental floss material being disposed between said two series of depressible cogs whereby when said strands of dental floss material are engaged and pulled transversely of said cog wheel, said cogs effect a change of direction of said dental floss material to form said loops.

8. The combination according to claim 5 in which a back-up wheel is rotatably mounted in association with said rotary member whereby the outer periphery of said back-up wheel is in engagement with the outer periphery of said rotary member and said first tape member is disposed between said rotary member and said back-up wheel with the adhesive side of said tape disposed toward said rotary member.

9. The combination according to claim 5, in which tape alignment means are provided over which said first tape member passes after said strands of dental floss material have become adherent thereto.

10. The combination according to claim 5, in which source means are provided for supplying said second tape member having adhesive thereon, and means for pressing the adhesive surfaces of said two tapes together to form a composite laminated tape between which selected portions of said dental floss filaments are secured.

11. The combination according to claim 5, in which means are provided including a pressure roller assembly and a perforator assembly for cutting said transverse slits in said tape which may be pulled apart upon the imposition of a predetermined amount of tensile force.

12. The combination according to claim 5, in which means are provided for cutting said tape at predetermined lengths.

13. The combination according to claim 5, in which said means for engaging said spaced and parallel strands of dental floss material as said strands are imposed on the outer periphery of said rotary member include a pair of oppositely facing spider wheels on each of which is pivotally mounted a multiplicity of reciprocable members including a hook portion for engaging an associated dental floss filament, and a stationary cam member including a cam surface adapted to be engaged by said reciprocable members when said spider wheels rotate to effect reciprocable action of said reciprocable members to effect engagement and subsequent disengagement of each associated filament upon predetermined rotation of said spider wheel.

14. The combination according to claim 5, in which said rotary member comprises a circular cog wheel, two circumferentially arranged series of depressible cogs supported on said cog wheel each of said cogs projecting from the surface of said cog wheel over a predetermined portion of its periphery and periodically being depressed during rotation thereof whereby said filaments of dental floss material may disengage themselves from said rotary member and remain attached to said tape member.

15. The combination according to claim 5, in which a cut-off wheel is provided for cutting said continuous chain into predetermined lengths each containing sixty-four loops of said dental floss material.

16. The combination according to claim 5, in which said means for imposing and adhesively adhering a first adhesive tape member to said pair of dental floss filaments includes a first freely rotatable source roll of said adhesive tape, and adhesive tape guide means embracing the outer peripheral edge portion of said source roll of adhesive tape whereby said tape is stripped from said source roll in precise alignment with said rotatable member upon which said pair of dental floss filaments are disposed in spaced parallel juxtaposition.

17. The combination according to claim 5, in which said means for imposing on said first tape member a second tape member includes a second freely rotatable source roll of said adhesive tape, and adhesive tape guide means embracing the outer peripheral edge portion of said source roll of adhesive tape whereby said tape is stripped from said source roll in precise alignment with said first adhesive tape member whereby the lateral edges of said first and second adhesive tape members are in precise alignment.

18. The combination according to claim 9, in which said tape alignment means comprises a pair of independently rotatable truncated right conical members in juxtaposition mounted on axes that are angularly disposed to each other and in a common plane whereby adjacent conical surfaces of said truncated right conical members define a crown therebetween upon which said first adhesive tape member impinges and by which said first adhesive tape member is maintained in precise alignment.

19. In a device for continuously dispensing an indeterminate length of tape from a source roll thereof, the combination comprising:
(a) a source roll of said tape including a hub upon which said tape is wound to define a roll having an outer peripheral surface from which said tape is unwound, said source roll being mounted for free rotation about a central axis and for free floatation axially of said central axis; and
(b) means including a tape guide roller including peripheral flanges adapted to snugly embrace and rotatably guide a peripheral edge portion of said source roll, whereby tape may be stripped from said source roll in precise alignment with said peripheral flanges.

20. An alignment device for maintaining the precise alignment of tape stripped from a source roll thereof and caused to move continuously, the combination comprising:
(a) a first truncated right conical member freely rotatable about a central axis; and
(b) a second truncated right conical member freely rotatable about a central axis;
(c) the central axes of said right conical members being angularly disposed one with the other but in a common plane whereby one peripheral edge portion of said truncated right conical members lie closely adjacent one another while the diametrically opposed peripheral edge portions are spaced further apart, whereby a crown is provided over which said tape may pass.

* * * * *